United States Patent
Sandu et al.

(10) Patent No.: US 9,038,451 B2
(45) Date of Patent: May 26, 2015

(54) OPTICAL METHOD FOR DETERMINING FOULING OF CRUDE AND HEAVY FUELS

(75) Inventors: Corina L. Sandu, Pearland, TX (US);
Sebatian Csutak, Houston, TX (US);
Marco Respini, Casalmorano (IT);
Huzeifa Ismail, Houston, TX (US);
Michael O. Brauchle, Madrid (ES)

(73) Assignee: Baker Hughes Incorporated, Houston, TX (US)

( * ) Notice: Subject to any disclaimer, the term of this patent is extended or adjusted under 35 U.S.C. 154(b) by 167 days.

(21) Appl. No.: 13/151,951

(22) Filed: Jun. 2, 2011
(Under 37 CFR 1.47)

(65) Prior Publication Data
US 2012/0125087 A1 May 24, 2012

Related U.S. Application Data

(60) Provisional application No. 61/362,430, filed on Jul. 8, 2010.

(51) Int. Cl.
*G01N 21/85* (2006.01)
*G01N 21/41* (2006.01)
*G01N 33/28* (2006.01)
*G01N 21/84* (2006.01)

(52) U.S. Cl.
CPC ........ *G01N 21/8507* (2013.01); *G01N 33/2823* (2013.01); *G01N 2021/8405* (2013.01)

(58) Field of Classification Search
USPC ............ 73/53.01, 53.05, 53.07, 61.63, 61.65, 73/152.01–152.58
See application file for complete search history.

(56) References Cited

U.S. PATENT DOCUMENTS

| | | | |
|---|---|---|---|
| 4,628,204 A | | 12/1986 | Maes |
| 4,882,499 A | | 11/1989 | Luukkala et al. |
| 5,157,339 A | * | 10/1992 | Scott et al. .................... 324/640 |
| 5,265,460 A | * | 11/1993 | Ellinger et al. ............... 73/32 R |
| 5,325,170 A | * | 6/1994 | Bornhop ....................... 356/128 |
| 5,363,696 A | * | 11/1994 | Cardellini et al. ........... 73/61.44 |
| 5,369,368 A | * | 11/1994 | Kassen et al. ................ 324/632 |
| 5,481,904 A | | 1/1996 | Fleck, Sr. et al. |
| 5,483,171 A | * | 1/1996 | Hatton et al. ................. 324/640 |
| 5,744,971 A | * | 4/1998 | Chan et al. .................... 324/643 |
| 6,467,340 B1 | * | 10/2002 | Gallagher et al. ......... 73/152.18 |

(Continued)

FOREIGN PATENT DOCUMENTS

DE    10225716 A1 *  1/2004  ............ F01M 11/10

OTHER PUBLICATIONS

Goual et al., "Measuring Asphaltenes and Resins. and Dipole Movement in Petroleum Fluids", American Institute of Chemical Engineering Journal, vol. 48, No. 11, Nov. 2002.*

(Continued)

*Primary Examiner* — David A Rogers
(74) *Attorney, Agent, or Firm* — Mossman, Kumar & Tyler, P.C.

(57) ABSTRACT

A method for detecting the formation of at least one phase in a mixture, particularly a hydrocarbon mixture. The method may include using a probe to expose a portion of the mixture to electromagnetic radiation to determine the value of a parameter of interest indicative of the formation of a phase. The method may also include using the value of the parameter of interest with a correlation between a known property of the mixture and the value of a parameter of interest to detect the formation of a phase.

32 Claims, 5 Drawing Sheets

(56) References Cited

U.S. PATENT DOCUMENTS

| | | | |
|---|---|---|---|
| 6,820,483 B1* | 11/2004 | Beckerman | 73/304 C |
| 6,839,137 B2 | 1/2005 | Mason et al. | |
| 7,016,026 B2* | 3/2006 | DiFoggio et al. | 356/128 |
| 7,091,719 B2* | 8/2006 | Freedman | 324/303 |
| 7,115,847 B2* | 10/2006 | Kinzer | 219/772 |
| 7,475,593 B2* | 1/2009 | Odom | 73/152.55 |
| 7,482,811 B2* | 1/2009 | Freedman | 324/324 |
| 7,751,044 B2 | 7/2010 | Csutak | |
| 7,782,460 B2* | 8/2010 | DiFoggio et al. | 356/409 |
| 7,927,479 B2 | 4/2011 | Greaney et al. | |
| 2002/0157991 A1 | 10/2002 | Mason et al. | |
| 2004/0055745 A1* | 3/2004 | Georgi et al. | 166/250.02 |
| 2005/0262936 A1* | 12/2005 | DiFoggio | 73/152.18 |
| 2005/0264302 A1* | 12/2005 | Mohajer et al. | 324/639 |
| 2008/0307860 A1* | 12/2008 | Guieze et al. | 73/61.44 |
| 2010/0020325 A1 | 1/2010 | Osaki et al. | |
| 2010/0096552 A1 | 4/2010 | Sharpe | |
| 2013/0009048 A1* | 1/2013 | Xie et al. | 250/256 |

OTHER PUBLICATIONS

Goual et al., Effect of Resins and DBSA on Asphaltene Precipitation from Petroleum Fluids, American Institute of Chemical Engineering Journal, vol. 50, No. 2, Feb. 2004.*

Buckley, J.S., et al., "Asphaltene Precipitation and Solvent Properties of Crude Oils," Petroleum Science and Technology, 16, No. 3-4, pp. 251-285 (1998).

* cited by examiner

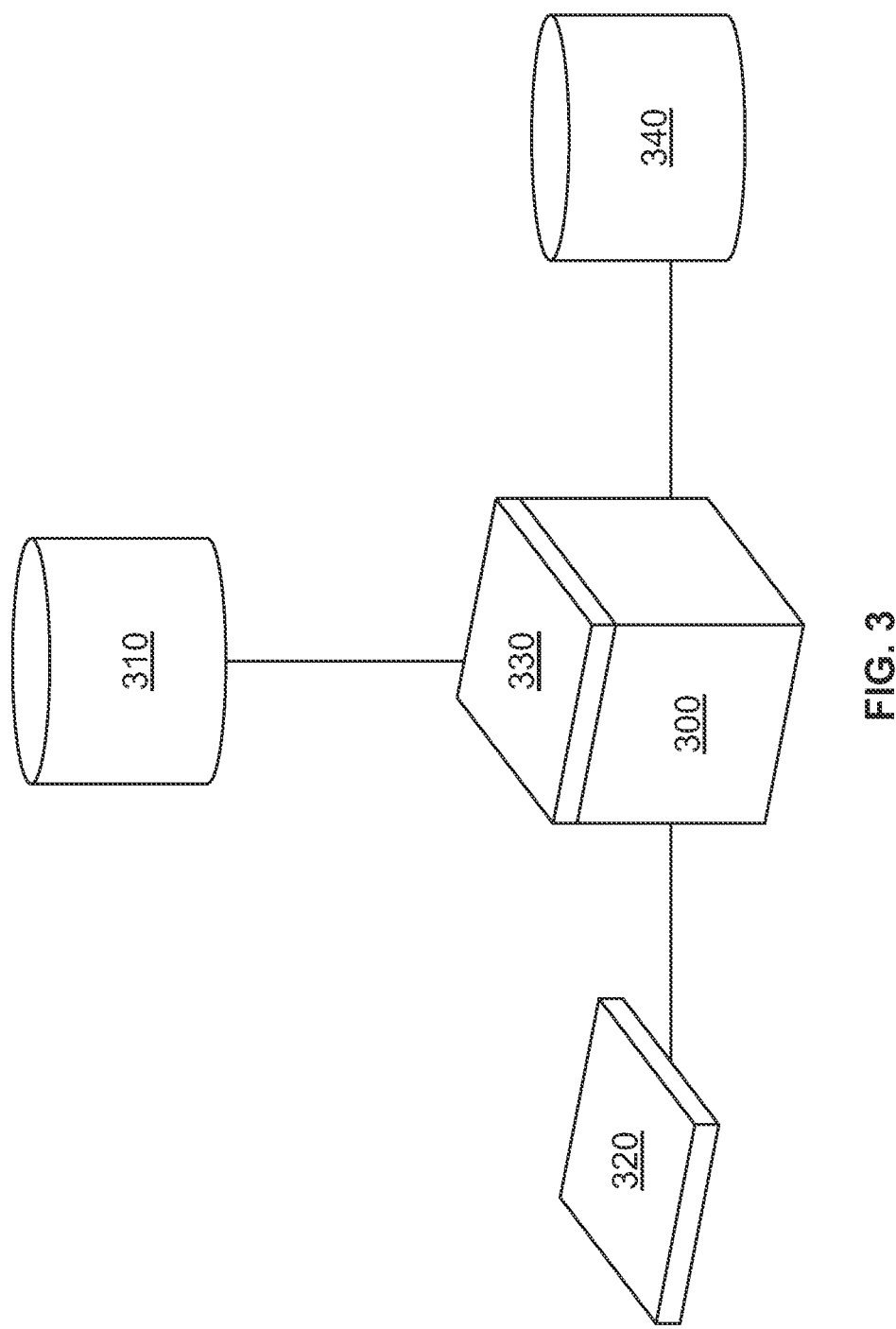

OPTICAL METHOD FOR DETERMINING FOULING OF CRUDE AND HEAVY FUELS

CROSS-REFERENCES TO RELATED APPLICATIONS

This application claims priority from U.S. Provisional Patent Application Ser. No. 61/362,430, filed on 8 Jul. 2010, the disclosure of which is incorporated herein by reference in its entirety.

FIELD OF THE DISCLOSURE

This disclosure generally relates to transportation, storage and mixing of hydrocarbons and, in particular, detecting solubility changes within a hydrocarbon mixture.

BACKGROUND OF THE DISCLOSURE

Hydrocarbon mixtures, such as crude oils and heavy fuel oils, with a general phase may be subject to physical properties changes such as solubility due to a series of operational parameters, such as temperature, pressure, and blending with different fluids such as hydrocarbon mixtures, water, and other liquids that may adversely affect the solubility of the resulting mixture, etc. Hydrocarbon mixtures may include hydrocarbons that may form hydrates when exposed to a variety of conditions, particularly a combination of lower temperature and higher pressure, in the presence of water. Hydrate solids (or crystals) may cause plugging and/or blockage of pipelines or transfer lines or other conduits, valves and/or safety devices and/or other equipment, resulting in shutdown, loss of production and risk of explosion or unintended release of hydrocarbons into the environment either on-land or off-shore.

Hydrocarbon hydrates are clathrates, and are also referred to as inclusion compounds. Clathrates are cage structures formed between a host molecule and a guest molecule. A hydrocarbon hydrate generally is composed of crystals formed by water host molecules surrounding the hydrocarbon guest molecules. The smaller or lower-boiling hydrocarbon molecules, particularly $C_1$ (methane) to $C_4$ hydrocarbons and their mixtures, are more problematic because it is believed that their hydrate or clathrate crystals are easier to form. For instance, it is possible for ethane to form hydrates at as high as 4° C. at a pressure of about 1 MPa. If the pressure is about 3 MPa, ethane hydrates can form at as high a temperature as 14° C. Even certain non-hydrocarbons such as carbon dioxide, nitrogen and hydrogen sulfide are known to form hydrates under the proper conditions.

Solubility variations in hydrocarbon mixtures may have objectionable effects on the mixture as a whole, such as when impurities drop out of the general phase to form undesirable precipitates, such as flocculation of asphaltenes (forming the additional phase), such as fouling scale deposits, etc. These impurities may precipitate out of the mixture or remain suspended. While remaining as an additional phase, the impurities may aggregate into substantial masses that may foul piping, storage facilities, and processing units as well as degrade the quality of the mixture. When a hydrocarbon mixture has formed an additional phase with objectionable properties, the mixture may be characterized as "unstable" or as "demonstrating instability."

Additives may be introduced to hydrocarbon mixtures to prevent or inhibit formation or aggregation of the additional phase (such as flocculated asphaltenes) and to restore stability to the hydrocarbon mixture. However, detection of formation of an additional phase generally must occur quickly to avoid aggregation of the additional phase into a substantial mass. On the other hand, since the additive is likely to be relatively expensive, the decision to introduce an additive, and a minimum appropriate amount of the additive, should be made judiciously. Hence, it is desirable to continuously monitor hydrocarbon mixtures for the aggregation of asphaltenes, and other substances that may form substantial masses within the hydrocarbon mixture, so that additives may be introduced quickly to mitigate problems due the flocculation of substances and their aggregation. It is also desirable to control or prevent the formation of an additional phase by identifying ratios of blend components such that stability of the hydrocarbon mixture is preserved.

SUMMARY OF THE DISCLOSURE

In aspects, this disclosure generally relates to transportation, storage, and mixing of hydrocarbons involving, particularly monitoring, hydrocarbons for preventing, mitigating, and monitoring the formation of phases that may result in fouling and/or instability.

One embodiment according to the present disclosure may include a method for detecting phase formation in a hydrocarbon mixture comprising: detecting formation of a second phase in the hydrocarbon mixture with a first phase using data from a probe and a known property of the hydrocarbon mixture.

Another embodiment according to the present disclosure may include a computer-readable medium product having stored thereon instructions that, when executed by at least one processor, perform a method, the method comprising: detecting formation of a second phase in a hydrocarbon mixture with a first phase using data from a probe and a known property of the hydrocarbon mixture.

Another embodiment according to the present disclosure may include a method for detecting phase formation in a hydrocarbon mixture, comprising: detecting formation of a second phase in a substance with a first phase by comparing a change in a parameter of interest of the hydrocarbon mixture, estimated by a probe, by a selected threshold.

Examples of the more important features of the disclosure have been summarized rather broadly in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein:

FIG. 3 is a schematic of a computer-readable medium configured to execute a method according to one embodiment of the present disclosure.

DETAILED DESCRIPTION OF THE DISCLOSURE

Figure 1A:
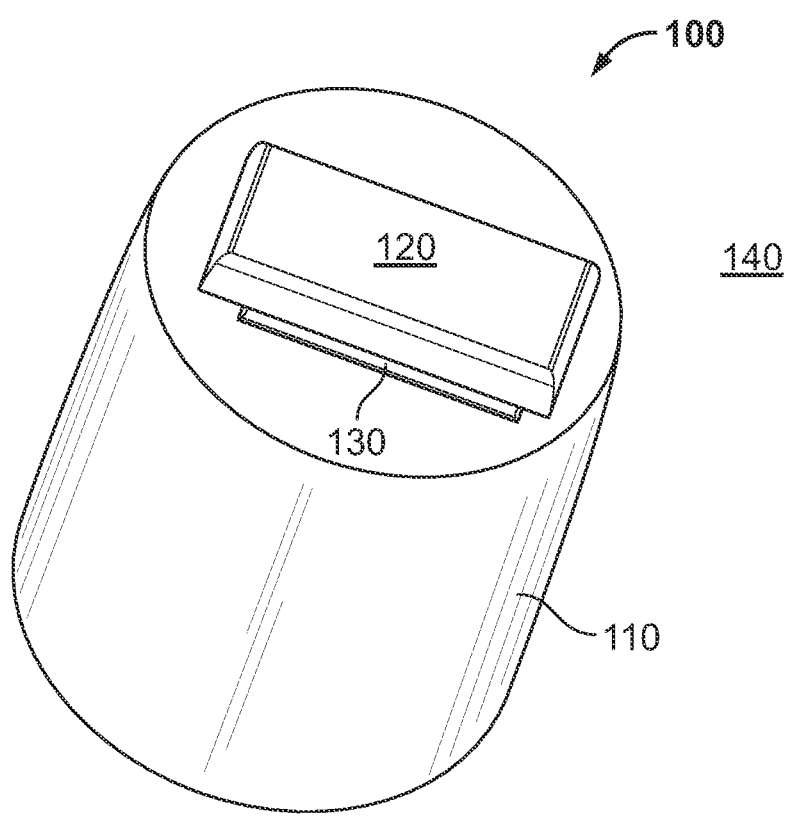
FIG. 1A is a schematic of an exemplary embodiment of a probe according to one embodiment of the present disclosure.

The present disclosure relates to methods and apparatuses for detecting the formation of phases in hydrocarbons that may cause or lead to fouling of a hydrocarbon mixture. The present disclosure also relates to methods and apparatuses for preventing the formation of phases in hydrocarbons. The hydrocarbon mixture, when fouled, may be viewed as a colloidal suspension, wherein the colloidal suspension may have two phases: an internal phase of solids or other matter, and a continuous phase that suspends the solids or other matter. The continuous phase of the colloidal suspension may be similar to the general phase or "first phase" of the hydrocarbon mixture prior to formation of an additional phase, also called herein an "internal phase" or "second phase." Herein "fouling" refers to the undesirable formation of an internal phase within the continuous phase of the hydrocarbons. In other aspects, the hydrocarbon mixture, when fouled, may take on the characteristics of a solution undergoing precipitation, again with an internal phase of solids at least temporarily suspended by a continuous phase. With fouling, the internal phase may demonstrate objectionable properties, such as high viscosity, clumping, and aggregation. Internal phases formed in hydrocarbon mixtures may include, but are not limited to, asphaltenes, scale, solids, polynuclear aromatics, and hydrocarbon hydrates. An internal phase may be formed by several mechanisms including, but not limited to, precipitation, aggregation, matrix destabilization, nucleation, solubility changes and coagulation.

The internal phase may demonstrate properties different from the properties of the continuous phase, and these differences may be identified optically, such as by absorption or diffusion of electromagnetic radiation. Detection of fouling may be performed by analyzing a parameter of interest of the hydrocarbons. Parameters of interest may include, but are not limited to, relative permittivity, refractive index, dielectric constant, electrical conductivity, ultrasound scattering, viscosity, electromagnetic radiation absorption, electromagnetic radiation diffusion, stability of continuous phase, optical or microscopical detection of the formation of the internal phase, absorption changes, conductivity, and viscosity. One of skill in the art with the benefit of this disclosure will see that the parameters of interest may be used to identify internal phase formations in fluids that are: (i) non-hydrocarbon mixtures, (ii) only partially made up of hydrocarbons, and (iii) non-mixtures whether containing hydrocarbons or not.

In some embodiments, the parameter of interest of a substance may be the refractive index. A refractive index, n, of a medium may be defined as the ratio of the speed, c, of a wave phenomenon, such as electromagnetic radiation or sound, in a reference medium to the phase speed, $v_p$, of the wave in the medium in question:

$$n = \frac{c}{v_p}. \quad (1)$$

In the context of electromagnetic radiation, $$n = \sqrt{\epsilon_r \mu_r} \quad (2)$$

where $\epsilon_r$ is the relative permittivity of the medium and $\mu_r$ is the relative permeability of the medium. For most materials, $\mu_r$ is close to 1, however, $\epsilon_r$ may vary with temperature, pressure, and chemical changes. Since $\mu_r$ may be relatively uniform, for some substances, changes in the relative permittivity, $\epsilon_r$, may be used to identify the formation of an internal phase.

Relative permittivity of a substance may have complex characteristics, such that relative permittivity may be expressed in terms of a real component and an imaginary component, when an electromagnetic field with frequency $\omega$ is applied to the substance. The complex permittivity may be expressed as:

$$\hat{\epsilon}(\omega) = \epsilon'(\omega) + i\epsilon''(\omega) \quad (3)$$

where $\epsilon''$ is the imaginary part of the relative permittivity, which is related to the dissipation (or loss) of energy within the medium, and $\epsilon'$ is the real part of the relative permittivity, which is related to the stored energy within the medium. In some embodiments, the formation of an internal phase may be detected by a change in the real component of relative permittivity. The real part of the permittivity may be obtained from the signal intensity change in the interference pattern. This signal can be monitored and correlated with the imaginary part of the permittivity.

In real materials, the polarization does not respond instantaneously to an applied field. This causes dielectric loss, which can be expressed by a permittivity that is both complex and frequency dependent. Real materials are not perfect electrical insulators either (i.e. they have non-zero direct current conductivity). Taking both aspects into consideration, a complex index of refraction can be defined:

$$\tilde{n} = n + i\kappa$$

Here, n is the refractive index indicating the phase speed, while κ is called the extinction coefficient, which indicates the amount of absorption loss when the electromagnetic wave propagates through the material. Both n and K are dependent on the frequency (wavelength). Note that the sign of the complex part is a matter of convention, which is important due to possible confusion between loss and gain.

Figure 1B:
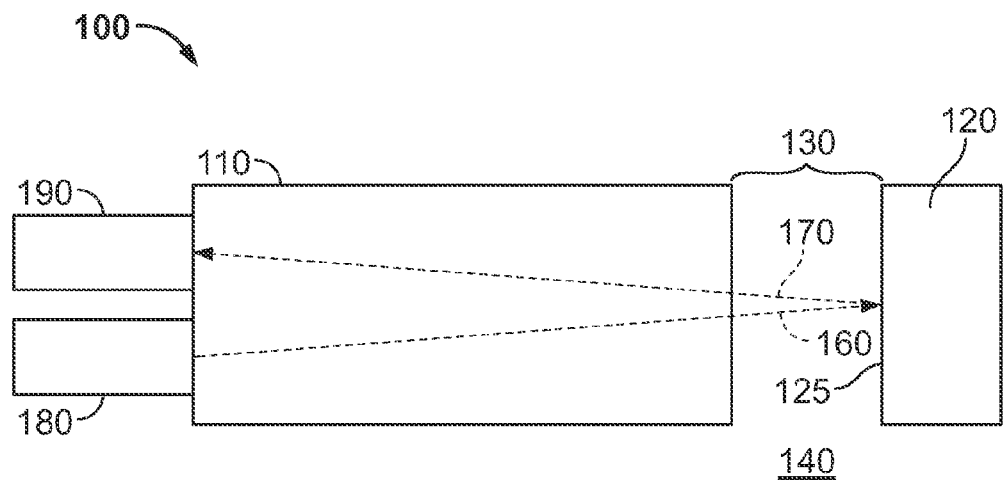
FIG. 1B is a schematic side view of the exemplary embodiment in FIG. 1A.

FIG. 1A shows an exemplary embodiment of a probe for detecting a value of a parameter of interest according to the present disclosure. The probe 100 may include a housing or body 110 that may contain, or serve as, a conduit for an electromagnetic source 180 (FIG. 1B). A reflector 120 may be disposed on the housing 110 such that electromagnetic radiation may be reflected back into the housing 110 after passing through a gap 130 between the housing 110 and reflector 120. The gap 130 is formed from at least one open space between the housing 110 and the reflective surface 125 of reflector 120 such that fluid 140 may intervene between the electromagnetic radiation and the reflector 120. Fluid 140 may be a mixture that includes one or more of: (i) a hydrocarbon and (ii) a non-hydrocarbon. The housing 110 may also contain a sensor 190 (FIG. 1B) to measure the reflected electromagnetic signal that has passed through fluid 140 across gap 130 and returned across gap 130 after contacting reflector 120. In some embodiments, housing 110 may include an optical cable. Herein, "optical" refers to the electromagnetic domain, including, but not limited to, visible light, infrared light, and ultraviolet light, together with coherent and incoherent light. In some embodiments, a sensor (not shown), replacing or in addition to sensor 190, may be disposed next to or replace reflector 120, such that one path of the electromagnetic radiation only passes through fluid 140 once before reaching a sensor (not shown). Gap 130 may be formed by one or more slits, holes, or other passages in the reflector 120, housing 110, both, or by a disposing the reflector 120 and housing 110 so as to leave a space between them. In some embodiments, gap 130 may be dimensioned to allow free flow of fluid 140 between housing 110 and reflector 120. In some embodiments, gap 130 may be dimensioned such that capillary action may draw a portion of fluid 140 into gap 130. In one embodiment, gap 130 may be dimensioned to have a narrow dimension of about 16 micrometers across, in a non-limiting embodiment. Gap 130 may be dimensioned based on the coherence length of the electromagnetic signal generated by electromagnetic source 180. Indeed, it was surprisingly discovered that a probe 100 having a very small slit or gap 130 on the order of only about 16 micrometers across was able to draw within it relatively viscous mixtures such as crude oil, heavy crude oil, #6 oils, diesel oil, bunker fuel oil, and fuel oil. In some embodiments, gap 130 may not be uniform in depth across its length and/or width. In some embodiments, the gap 130 may be dimensioned based on the intensity or frequency of electromagnetic radiation generated by electromagnetic source 180. In some embodiments, electromagnetic source 180 may generate one or more of: (i) a coherent light beam, (ii) a collimated light beam, and (iii) a non-collimated light beam.

FIG. 1B shows another orientation of the exemplary embodiment 100 from FIG. 1A. In FIG. 1B, electromagnetic source 180 and sensor 190 are shown disposed at one end of housing 110. A light beam 160 emitted from electromagnetic source 180 is shown passing through fluid 140 in gap 130 to be reflected by reflector 120. The reflected beam 170 then passes through fluid 140 in gap 130 to reach sensor 190. Housing 110 may be hollow or partially or completely filled with one or more substances that are transparent to the passage of the electromagnetic beams 160. The positions of electromagnetic source 180 and sensor 190 are illustrative and exemplary only, as the electromagnetic source 180 and/or sensor 190 may be disposed within housing 110 or in another position relative to the housing 110. Electromagnetic source 180 may be configured to generate an electromagnetic beam 160 that may be responsive to fluid 140 such that the electromagnetic beam 160 may respond differently to the internal phase of fluid 140 than to the continuous phase of fluid 140. In some embodiments, electromagnetic source 180 may be configured to generate electromagnetic beam 160 such that the continuous phase of fluid 140 may be transparent or almost transparent to electromagnetic beam 160. Herein, the use of the term "beam" may be construed as meaning emitted light and does not imply that the electromagnetic radiation must be concentrated, focused, coherent, or collimated. In some embodiments, fluid 140 may be a mixture. In some embodiments, fluid 140 may be a hydrocarbon mixture, including, but not limited to, one or more of: (i) a crude oil, heavy crude oil, (ii) a heavy fuel oil or #6 oils, (iii) a diesel oil, and (iv) a bunker fuel oil. In some embodiments, fluid 140 may include a substance that may form a gas hydrate, such as, but not limited to, a hydrocarbon hydrate. In some embodiments, the fluid 140 may be flowing through gap 130 or stagnant.

Figure 1C:
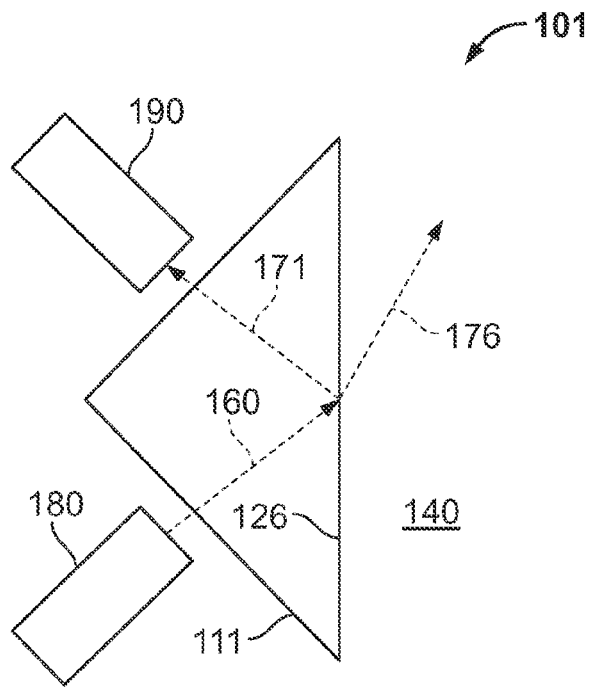
FIG. 1C is a schematic side view of another exemplary embodiment of a probe according to own embodiment of the present disclosure.

FIG. 1C shows another embodiment, probe 101, according to the present disclosure. Probe 101 may include a housing or body 111 configured as a conduit for an electromagnetic beam 161 from an electromagnetic source 180. Electromagnetic source 180 and sensor 190 may be disposed along housing 111. Housing 111 is at least partially transparent to an electromagnetic beam 161 emitted from electromagnetic source 180 and includes, at least in part, a material with a refractive index that is higher than fluid 140, such that at least part of electromagnetic beam 161 is at least partially internally reflected at the interface 126 between body 111 and fluid 140 to form reflected electromagnetic beam 171, while the remainder of electromagnetic beam 161 is refracted into the fluid 140 as electromagnetic beam 176. One example of a body and sensor combination as envisioned in this disclosure is the K-PATENTS™ Refractometer Model No. PR-23-GP. The use of a triangular prism as housing 101 is exemplary and illustrative only, as embodiments according to the present disclosure may be realized with other shapes of prismatic objects (polygonal and non-polygonal), including prismatic objects with more than one interface configured to cause internal reflections (trapezoidal shapes, spheres, etc.).

Figure 2A:
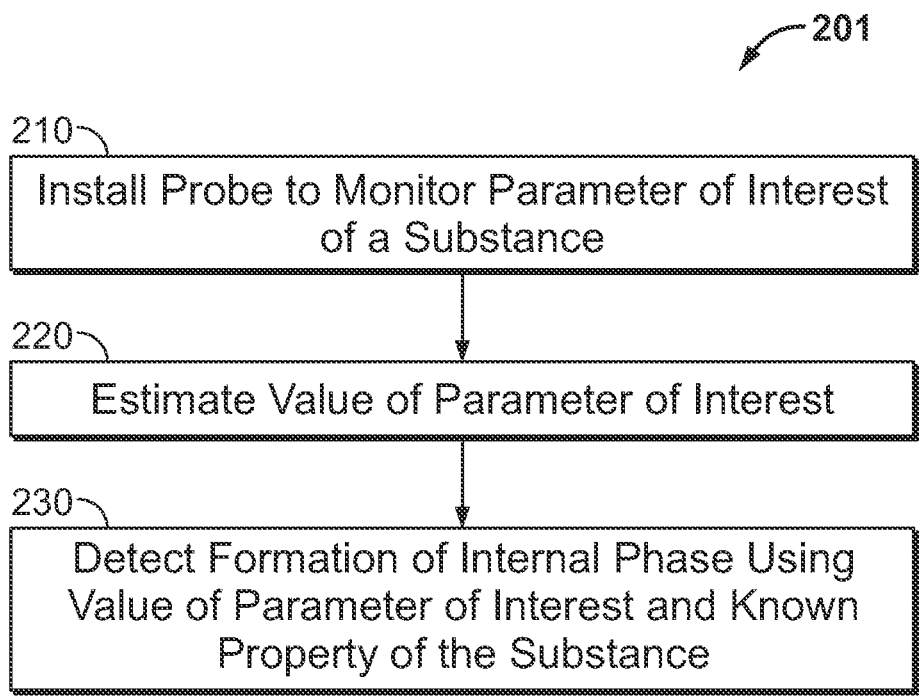
FIG. 2A shows a method according to one embodiment of the present disclosure.

FIG. 2A shows an exemplary method 201 for using the probe 100 to detect the formation of an internal phase. In step 210, probe 100 may be installed in a fluid 140. Fluid 140 may be a mixture containing at least one hydrocarbon, alcohol, or glycol. Installation may be permanent or temporary, and probe 100 may be stationary or in motion after installation. In other alternative embodiments, the probe 100 may be retractable, for instance, when in operation inserted or placed into the flow in a pipeline or into a mixture stored in a tank, and then retracted for cleaning, calibration, replacement or other service. In step 220, probe 100 may estimate the value of a parameter of interest of the fluid 140 that occupies the gap 130 between housing 110 and reflector 120. In step 230, the estimated value of the parameter of interest may be combined with a known property of the fluid 140 to determine if an internal phase has formed or is in the process of forming. Estimating the value of the parameter of interest of the fluid may be performed once, continuously, or periodically. In some embodiments, step 210 may not need to be performed. In some embodiments, if an internal phase has formed or is in the process of forming, the method 201 may include adding a chemical additive or changing temperature/pressure to the fluid 140 to reduce or eliminate the internal phase. In some embodiments, the method 201 may include the step of detecting the reduction or elimination of an internal phase using a value of the parameter of interest of the fluid 140. In some embodiments, the method 201 may include the step of adjusting an amount of additive added to the fluid 140 based the value of the parameter of interest of the fluid 140. In some embodiments, the known property of fluid 140 may be a correlation between the formation of an internal phase a value of a parameter of interest. In some embodiments, the known property of the fluid may be correlated with the formation of an internal phase through experimental trials. In some embodiments, the correlation may be established by performing a test on fluid 140 or a substantially similar sample, using as the testing technique, but not limited to, one of: (i) p testing, (ii) titration, and (iii) optical detection. Herein, p-testing means the determination of a p-value as an indicator of stability of a hydrocarbon containing fluid. P-value is the ratio of precipitating paraffins to oil (volume/mass) necessary to generate phase separation of foulants (such as asphaltenes). P-testing may include adding n-cetane to a vistar (visbroken tar and/or vacuum residuum) or heavy fuel oil sample, heating and cooling the sample for specified periods of time, and evaluating the sample for microscopic flocculation/aggregation of asphaltenes.

Figure 2B:
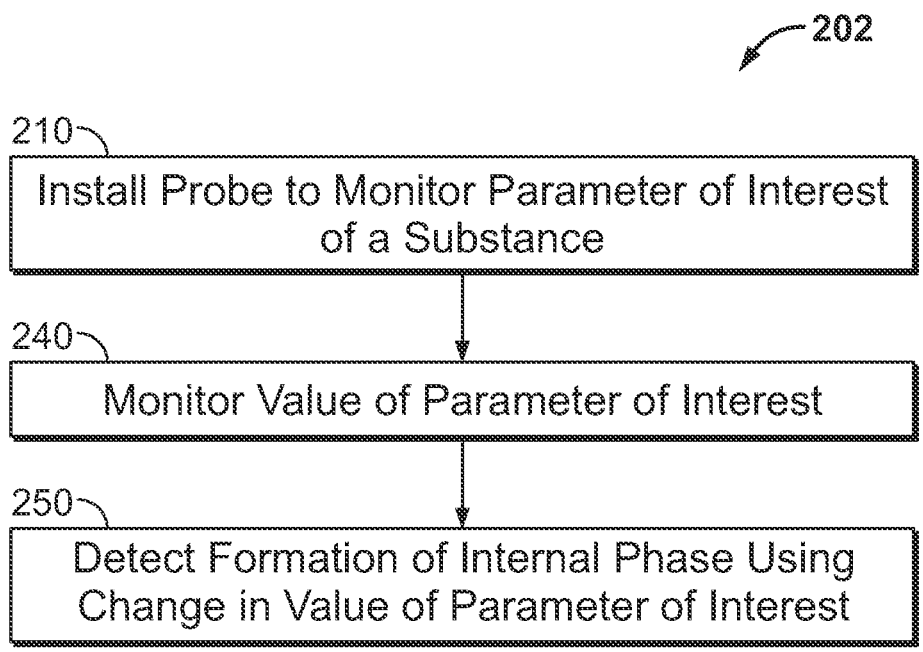
FIG. 2B shows another method according to an alternative embodiment of the present disclosure.

FIG. 2B, shows another exemplary method 202 for using probe 100 to detect the formation of an internal phase. In step 210, probe 100 may be installed in a fluid 140. Fluid 140 may be a mixture containing at least one hydrocarbon. Installation may be permanent or temporary, and probe 100 may be stationary or in motion after installation. In step 240, probe 100 may monitor the value of a parameter of interest of the fluid 140 that occupies the gap 130 between housing 110 and reflector 120. Monitoring may be performed continuously or periodically. In step 250, an estimated value of the parameter of interest compared with one or more previously estimated values of the parameter of interest to detect a change in the value of the parameter of interest that exceeds a selected amount or threshold. In some embodiments, the threshold may be established based on the refractive index of the fluid at various temperatures. In some embodiments, the threshold may be a change of refractive index of between about 0.001 to about 0.05 RI units. The selected amount may indicate that an internal phase has formed or is in the process of forming. One of skill in the art with the benefit of the information in the present disclosure will appreciate that the selected amount of change may vary for a particular fluid due to one or more properties of the fluid, including, but not limited to: composition, temperature, and pressure. In some embodiments, step 210 may not need to be performed. In some embodiments, step 250 may be performed by trending, graphing, or plotting the data obtained during step 240. In some embodiments, if an internal phase has formed or is in the process of forming, the method 202 may include adding an additive to the fluid 140 to reduce or eliminate the internal phase. In some embodiments, the method 201 may include the step of detecting the reduction or elimination of an internal phase using a value of the parameter of interest of the fluid 140. In some embodiments, the method 202 may include the step of adjusting an amount of chemical additive added to the fluid 140 based the value of the parameter of interest of the fluid 140.

In support of the teachings herein, various analysis components may be used, including digital and/or analog systems. The system may have components such as a detection, pumping system, flashing, processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present disclosure. These instructions may provide for equipment operation, control, data collection and analysis and other functions deemed relevant by a system designer, owner, user or other such personnel, in addition to the functions described in this disclosure.

As shown in FIG. 3, certain embodiments of the present disclosure may be implemented with a hardware environment that includes an information processor 300, a data storage medium 310, an input device 320, processor memory 330, and may include peripheral data storage medium 340. The input device 320 may be any data reader or user input device, such as data card reader, keyboard, USB port, etc. The data storage medium 310 stores formation characteristic data provided by a user or user system. Data storage medium 310 may be any standard computer data storage device, such as a USB drive, memory stick, hard disk, removable RAM, or other commonly used memory storage system known to one of ordinary skill in the art including Internet based storage. Data storage medium 310 stores a program that when executed causes information processor 300 to execute the disclosed method. Data storage medium 310 may also store the formation data provided by the user, or the formation data may be stored in a peripheral data storage medium 340, which may be any standard computer data storage device, such as a USB drive, memory stick, hard disk, removable RAM, or other commonly used memory storage system known to one of ordinary skill in the art including Internet based storage. Information processor 300 may be any form of computer or mathematical processing hardware, including Internet based hardware. When the program is loaded from data storage medium 310 into processor memory 330 (e.g. computer RAM), the program, when executed, causes information processor 300 to retrieve formation data from either data storage medium 310 or peripheral data storage medium 340 and process the formation data to characterize the formation.

Figure 4:
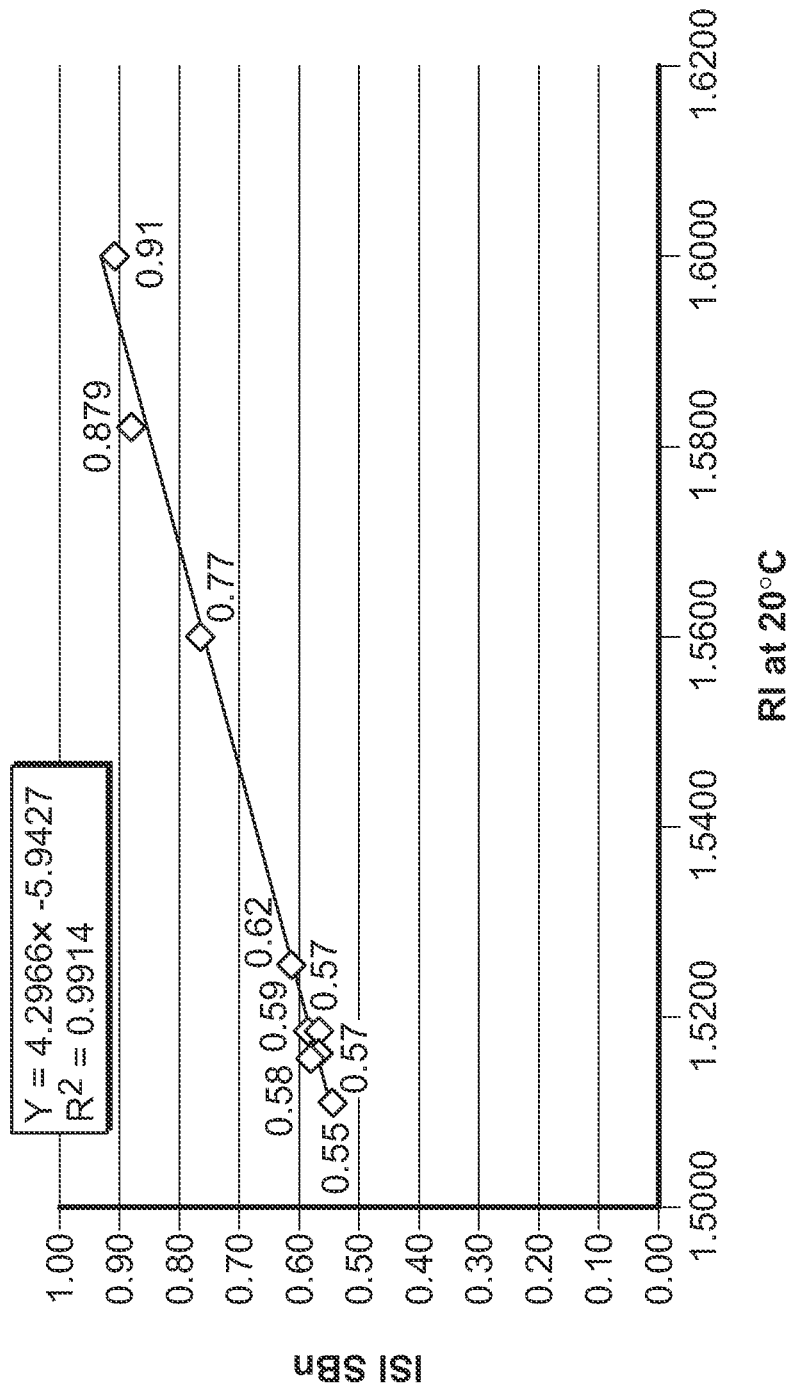
FIG. 4 shows an exemplary correlation between a parameter of interest and a known property of fluid.

FIG. 4 shows an exemplary correlation between a parameter of interest and a known property of fluid 140. Here, the parameter of interest is the refractive index (RI), which is correlated with an ISI Solubility Blending Number (ISI SBn) for fluid 140. In one embodiment, the refractive index data obtained by probe 100 may be used to determine the ISI Solubility Blending Number for the fluid 140, which corresponds to the stability of fluid 140. The ISI SBn refers to the result of a method for estimating the stability of fluid 140 that may employ a near infra-red source and detector, which may be used as an alternative to the p-method. The relationship between the ISI Solubility Blending Number and the formation of an internal phase may be established through experimentation or other techniques known to those of skill in the art with the benefit of the present disclosure. The use of the ISI Solubility Blending Number is exemplary and illustrative only, as other indicators (such as particle size changes, p-value stability, and titration-based methods) may be correlated with the formation of an internal phase.

In alternative embodiments, the methods herein may include the introduction of a chemical additive in response to detecting the formation of a second phase in the substance to inhibit or prevent the further formation of the second phase. Such chemical additives may include, but not necessarily be limited to, asphaltene inhibitors, scale inhibitors, hydrate inhibitors, dispersants, reactive agents, antifouling additives, and the like which are known in the art. In a different non-limiting embodiment, the conditions of the substance or mixture may be changed to inhibit or prevent formation of the second phase, including, but not necessarily limited to, changing the temperature, pressure, or composition of the substance or mixture (e.g. adding a solvent in addition to or instead of an inhibitor). In these ways, the stability of the substance or fluid may be improved.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the disclosure disclosed. For instance, the methods and apparatuses may be advantageously employed at some distance into a wellbore or along a pipeline (e.g. about 4 km or more). The probes and methods herein may be non-explosive. The methods and apparatuses may also be advantageously employed at relatively high temperatures, for instance up to 300° C., or even higher.

Further, the methods and apparatuses described will find particular use in mixing two or more different hydrocarbons, in a non-limiting example, two different crude oils, to detect the aggregation of asphaltenes or other second phases in the mixtures. It often happens that two or more crude oils may be stable at a particular temperature and pressure, but when mixed asphaltene precipitation may occur spontaneously. This may be because the asphaltene becomes destabilized and start to aggregate in species that are not as soluble in the mixture and thus form, flocculate, or precipitate only after mixing. The asphaltene-forming molecules may be kept from undesirably forming by Brownian motion, maltenes, aromatics, and more aromatic and polar containing species and forces which are likely disturbed upon mixing. There presently exist tests for detecting such asphaltene formation, but these tests may take many hours or even days to perform, whereas the apparatus and methods herein may give very fast (on the order of minutes or seconds) detection of aggregation of asphaltenes and other second phase formation in online or continuous stream applications.

While the disclosure has been described with reference to exemplary embodiments, it will be understood by those skilled in the art that various changes may be made and equivalents may be substituted for elements thereof without departing from the scope of the disclosure. In addition, many modifications will be appreciated by those skilled in the art to adapt a particular instrument, situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The words "comprising" and "comprises" as used throughout the claims is to be interpreted to mean "including but not limited to".

We claim:

1. A method for detecting phase formation in a hydrocarbon mixture using a probe comprising a housing, comprising:
installing the probe for operation in a flowing fluid comprising the hydrocarbon mixture such that an exterior of the housing is immersed in the flowing fluid, the probe configured to be retracted while not in operation; and
detecting in operation, in situ, formation of a second phase in the hydrocarbon mixture with a first phase using data from the probe and a known property of the hydrocarbon mixture, wherein the probe is responsive to an electromagnetic signal that has passed through a portion of the mixture across a gap in the probe; and
wherein the portion of the mixture enters the probe through the gap.

2. The method of claim 1 where the hydrocarbon mixture, is selected from at least one of the group consisting of: (i) a crude oil, (ii) a heavy crude oil, (iii) a heavy fuel oil, (iv) a #6 oil, (v) a diesel oil, and (vi) a bunker fuel oil.

3. The method of claim 1 where the second phase is selected from at least one of the group consisting of: (i) an aggregation of asphaltenes, (ii) scale, and (iii) a hydrocarbon hydrate.

4. The method of claim 1 where the data from the probe is a signal indicating a relative permittivity of the hydrocarbon mixture.

5. The method of claim 1 where the probe comprises:
a housing configured to at least partly transmit an electromagnetic beam and configured to be placed in contact with the hydrocarbon mixture;
an electromagnetic source configured to transmit an electromagnetic beam through the housing and toward the hydrocarbon mixture; and
a sensor positioned to receive a reflected electromagnetic beam from the housing.

6. The method of claim 1, further comprising:
changing at least one condition selected from the group consisting of: (i) the temperature of the hydrocarbon mixture, (ii) the pressure of the hydrocarbon mixture, and combinations thereof.

7. The method of claim 1, where the detection is performed continuously.

8. The method of claim 1, wherein the hydrocarbon mixture is flowing.

9. The method of claim 1, wherein the gap is less than 20 micrometers.

10. The method of claim 1, wherein the gap is configured to draw the portion of the mixture into the gap through capillary action.

11. The method of claim 1, wherein the gap is submerged in the flowing fluid and configured for free passage of the mixture into the gap from an exterior of the probe.

12. The method of claim 1, wherein positioning the probe in a flowing fluid comprises inserting the probe into a flow inside at least one of i) a wellbore; and ii) a pipeline.

13. The method of claim 1 where the known property is a correlation between formation of the second phase and a relative permittivity of the hydrocarbon mixture.

14. The method of claim 13, wherein the correlation is estimated using a parameter selected from the group consisting of: (i) p-testing, (ii) titration, and (iii) optical detection and combinations thereof.

15. The method of claim 1 where the probe comprises:
a housing;
an electromagnetic source disposed on the housing; and
a sensor disposed on the housing such that the hydrocarbon mixture is between the electromagnetic source and the sensor along a beam path;
wherein the gap comprises a slit in the housing.

16. The method of claim 15 where the electromagnetic source, is selected from at least one of the group consisting of: (i) visible light source, (ii) an infrared light source, and (iii) an ultraviolet light source.

17. The method of claim 15 where the electromagnetic source is a coherent light source.

18. The method of claim 1, further comprising:
adding an additive to the hydrocarbon mixture.

19. The method of claim 18, further comprising:
detecting an elimination of the second phase in the hydrocarbon mixture using data from the probe and the known property of the hydrocarbon mixture.

20. The method of claim 18, further comprising:
controlling an amount of the additive to be added to the hydrocarbon mixture based on data from the probe and the known property of the hydrocarbon mixture.

21. A non-transitory computer-readable medium product having stored thereon instructions that, when executed by at least one processor, perform a method, the method comprising:
extending a probe from a retracted position to an extended position within a flowing fluid;
detecting formation of a second phase in a hydrocarbon mixture with a first phase using data from a probe positioned in a flowing fluid comprising the hydrocarbon mixture and a known property of the hydrocarbon mixture, wherein the probe is responsive to an electromagnetic signal that has passed through a portion of the mixture across a gap in the probe, the portion of the mixture having entered the probe through the gap.

22. The non-transitory computer-readable medium product of claim 21, further comprising at least one of: (i) a ROM, (ii) an EPROM, (iii) an EEPROM, (iv) a removable RAM, (v) a flash memory, and (vi) an optical disk.

23. A method for detecting phase formation in a hydrocarbon mixture using a probe comprising a housing, comprising:
  installing the probe for operation in a flowing fluid comprising the hydrocarbon mixture such that an exterior of the housing is immersed in the flowing fluid, the probe configured to be retracted while not in operation; and
  detecting, in situ, formation of a second phase in the hydrocarbon mixture with a first phase by comparing a change in a parameter of interest of the hydrocarbon mixture, wherein the parameter of interest is estimated by the probe and the change exceeds a selected threshold.

24. The method of claim 23 where the hydrocarbon mixture, is selected from at least one of the group consisting of: (i) a crude oil, (ii) heavy crude oil, (iii) a heavy fuel oil, (iv) a diesel oil, and (v) a #6 oil, and (vi) a bunker oil.

25. The method of claim 23 where the second phase is selected from at least one of the group consisting of: (i) aggregated asphaltenes, (ii) scale, and (iii) a hydrocarbon hydrate.

26. The method of claim 23 where the parameter of interest is relative permittivity.

27. The method of claim 23, further comprising:
  controlling an amount of an additive to be added to the substance based on data from the probe and the known property of the hydrocarbon mixture;
  detecting an elimination of the second phase in the substance using data from the probe and the known property of the hydrocarbon mixture.

28. The method of claim 23, using, for the selected threshold, from about 0.001 to about 0.05 RI units.

29. A method for detecting phase formation in a hydrocarbon mixture using a probe comprising a housing, comprising:
  installing the probe for operation in a flowing fluid comprising the hydrocarbon mixture such that an exterior of the housing is immersed in the flowing fluid, the probe configured to be retracted while not in operation; and
  detecting, in situ, formation of a second phase in the hydrocarbon mixture with a first phase using data from the probe and a known property of the hydrocarbon mixture; and adding an additive inhibiting the second phase to the hydrocarbon mixture responsive to detecting the second phase.

30. The method of claim 29, further comprising controlling an amount of the additive added to the hydrocarbon mixture based on the data from the probe and the known property of the hydrocarbon mixture.

31. A method for detecting phase formation in a hydrocarbon mixture using a probe comprising a housing, comprising:
  detecting, in situ, formation of a second phase in the hydrocarbon mixture with a first phase using data from the probe and a known property of the hydrocarbon mixture, wherein the probe is responsive to an electromagnetic signal that has passed through a portion of the mixture across a gap in the probe, wherein the gap is configured to draw the portion of the mixture into the gap through capillary action.

32. A method for detecting phase formation in a hydrocarbon mixture using a probe comprising a housing, comprising:
  positioning the probe in a flowing fluid comprising the hydrocarbon mixture such that an exterior of the housing is immersed in the flowing fluid; and
  detecting, in situ, formation of a second phase in the hydrocarbon mixture with a first phase using data from the probe and a known property of the hydrocarbon mixture, wherein the probe is responsive to an electromagnetic signal that has passed through a portion of the mixture across a gap in the probe; and
  wherein the portion of the mixture enters the probe through the gap, and wherein the gap is less than 20 micrometers.

* * * * *